(12) United States Patent
Chovanda et al.

(10) Patent No.: US 9,710,604 B2
(45) Date of Patent: Jul. 18, 2017

(54) ANALYTE METER WITH OPERATIONAL RANGE CONFIGURATION TECHNIQUE

(71) Applicant: LifeScan, Inc., Milpitas, CA (US)

(72) Inventors: Sweta Chovanda, Exton, PA (US); Shawn Berven, Philadelphia, PA (US)

(73) Assignee: LifeScan, Inc., Wayne, PA (US)

( * ) Notice: Subject to any disclaimer, the term of this patent is extended or adjusted under 35 U.S.C. 154(b) by 520 days.

(21) Appl. No.: 13/929,761

(22) Filed: Jun. 27, 2013

(65) Prior Publication Data

US 2015/0006087 A1  Jan. 1, 2015

(51) Int. Cl.

| | |
|---|---|
| G01N 33/48 | (2006.01) |
| G01N 31/00 | (2006.01) |
| G06G 7/48 | (2006.01) |
| G06G 7/58 | (2006.01) |
| G06F 19/00 | (2011.01) |
| A61B 5/145 | (2006.01) |
| G01N 27/327 | (2006.01) |
| A61B 5/00 | (2006.01) |
| A61B 5/1468 | (2006.01) |
| A61B 5/15 | (2006.01) |
| A61B 5/157 | (2006.01) |

(52) U.S. Cl.
CPC ...... *G06F 19/3406* (2013.01); *A61B 5/14532* (2013.01); *A61B 5/7475* (2013.01); *G01N 27/3273* (2013.01); *A61B 5/1468* (2013.01); *A61B 5/157* (2013.01); *A61B 5/150022* (2013.01); *A61B 5/150358* (2013.01); *A61B 5/742* (2013.01); *A61B 2560/0431* (2013.01); *A61B 2562/0209* (2013.01)

(58) Field of Classification Search
None
See application file for complete search history.

(56) References Cited

U.S. PATENT DOCUMENTS

| | | |
|---|---|---|
| 2008/0172031 A1 | 7/2008 | Blomquist |
| 2009/0018779 A1 | 1/2009 | Cohen et al. |
| 2010/0137699 A1* | 6/2010 | Sher .......... A61B 5/14532 600/365 |
| 2012/0053843 A1 | 3/2012 | Tubb |
| 2012/0116196 A1 | 5/2012 | Tubb |

FOREIGN PATENT DOCUMENTS

| | | |
|---|---|---|
| WO | 2013098563 A1 | 7/2013 |
| WO | 2013098564 A1 | 7/2013 |
| WO | 2013098565 A1 | 7/2013 |

OTHER PUBLICATIONS

Application as filed for related U.S. Appl. No. 61/581,087, filed Dec. 29, 2011.
Application as filed for related U.S. Appl. No. 61/581,089, filed Dec. 29, 2011.

(Continued)

*Primary Examiner* — Larry D Riggs, II

(57) ABSTRACT

Described are techniques governing the glycemic ranges that are applied and governed in the meter so the user is not required to understand or know the editing rules in order to use or set up the meter. These guiding principles will come into effect each time the user chooses to edit the ranges. There will be appropriate warning messages to inform the user if the user does not set the ranges correctly.

7 Claims, 4 Drawing Sheets

(56) References Cited

OTHER PUBLICATIONS

Application as filed for related U.S. Appl. No. 61/581,099, filed Dec. 29, 2011.
Application as filed for related U.S. Appl. No. 61/581,100, filed Dec. 29, 2011.
Application as filed for related U.S. Appl. No. 61/654,013, filed May 31, 2012.
International Search Report and Written Opinion issued in related International Patent Application No. PCT/US2014/042640, dated Oct. 28, 2014, 9 pages.

* cited by examiner

ANALYTE METER WITH OPERATIONAL RANGE CONFIGURATION TECHNIQUE

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

For those with diabetes, part of managing the disease is knowing whether the measured glucose is within a desired range. Currently, there are glucose meters that provide for visual indication of whether a measured glucose result is within a desired glycemic range. While this may be helpful to the user, it is believed that there may be shortcomings for these meters when range is expanded to cover other glycemic states of the user.

SUMMARY OF THE DISCLOSURE

In a proposed blood glucose meter, three different range types can be utilized to indicate the glycemic states of the user. The range types that can be displayed are a "general" glycemic range, a "before meal" and an "after meal" range. A "before meal" range is a range of glucose values that the user should have prior to a meal. An "after meal" range is a range of glucose values that the user should have after a meal. The "after meal range" is preferably a range within about 2 hours after a meal. To allow these three ranges to be displayed against the same indicator key, the meter has default ranges against which an indicator is presented. The indicator moves between 3 indicia (e.g., in the form of 3 colors, red, green, and blue) to advise the user if they are below target in range or above target. During setup, the meter presents the user with default ranges that can be accepted as is. If the user decides to edit the default ranges, then there are certain rules that need to be followed in order to set and customize these ranges. This customization of the ranges in turn allows the range indicator to more accurately indicate where the current blood glucose ("BG") measurement or reading is in relation to the desired range settings (whether higher or within or lower than the desired range) as referenced against the discrete indicia (e.g., color) coded scale.

Applicants have recognized that these range editing rules can be confusing to the user. Consequently, applicants have devised three guiding principles governing the ranges be implemented in the meter so the user doesn't need to know the editing rules in order to use or set up the meter. These guiding principles will come into effect each time the user chooses to edit the ranges. There will be appropriate warning messages to inform the user if they aren't setting the ranges correctly.

Accordingly, applicants have devised a method of operating a glucose meter. The meter has a user interface and display operatively connected to a microprocessor and non-volatile memory. The method can be achieved by: entering into the microprocessor via an user interface and an input high value to define glucose values for an overall range of glucose values; in the event the input high value is entered as a value less than a preset minimum then the preset minimum is changed by the microprocessor to a new low value lower than the input high value or equal to a minimum permitted low value, wherein the new low value is stored in the non-volatile memory of the glucose meter; and in the event the input low value is entered as greater than a preset maximum value then the preset maximum value is changed by the microprocessor to a new high value greater than the input low value or equal to the maximum permitted high value, wherein the new low value is stored in the non-volatile memory of the glucose meter.

In another aspect, a method of operating a glucose meter is provided. The meter has a user interface and display operatively connected to a microprocessor and non-volatile memory. The method can be achieved by: entering into the microprocessor via an user interface at least one of an after meal low value for an after meal minimum and an after meal high value for an after meal maximum to define a range of glucose values associated with glucose measurements taken after a meal; in the event the after meal low value is entered as a value lower than a before meal minimum then annunciating an error and requesting the user via the user interface to change the after meal low value to a value higher than the before meal minimum; and in the event that the after meal high value is entered as a value lower than a before meal maximum then annunciating an error and requesting the user via the user interface to change the after meal high value to a value greater than the before meal maximum.

In yet a further aspect, a method of operating a glucose meter is provided. The meter has a user interface and display operatively connected to a microprocessor and non-volatile memory. The method can be achieved by: entering into the microprocessor via an user interface at least one of a before meal low value for a before meal minimum and a before meal high value for a before meal maximum to define a range of glucose values associated with glucose measurements taken before a meal; in the event the before meal low value is entered as a value higher than an after meal minimum then annunciating an error and requesting the user via the user interface to change the before meal low value to a value less than the after meal minimum; and in the event the before meal high value is entered as a value higher than the after meal maximum then annunciating an error and requesting the user via the user interface to change the before meal high value to a value less than the after meal maximum.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably.

Figure 1:
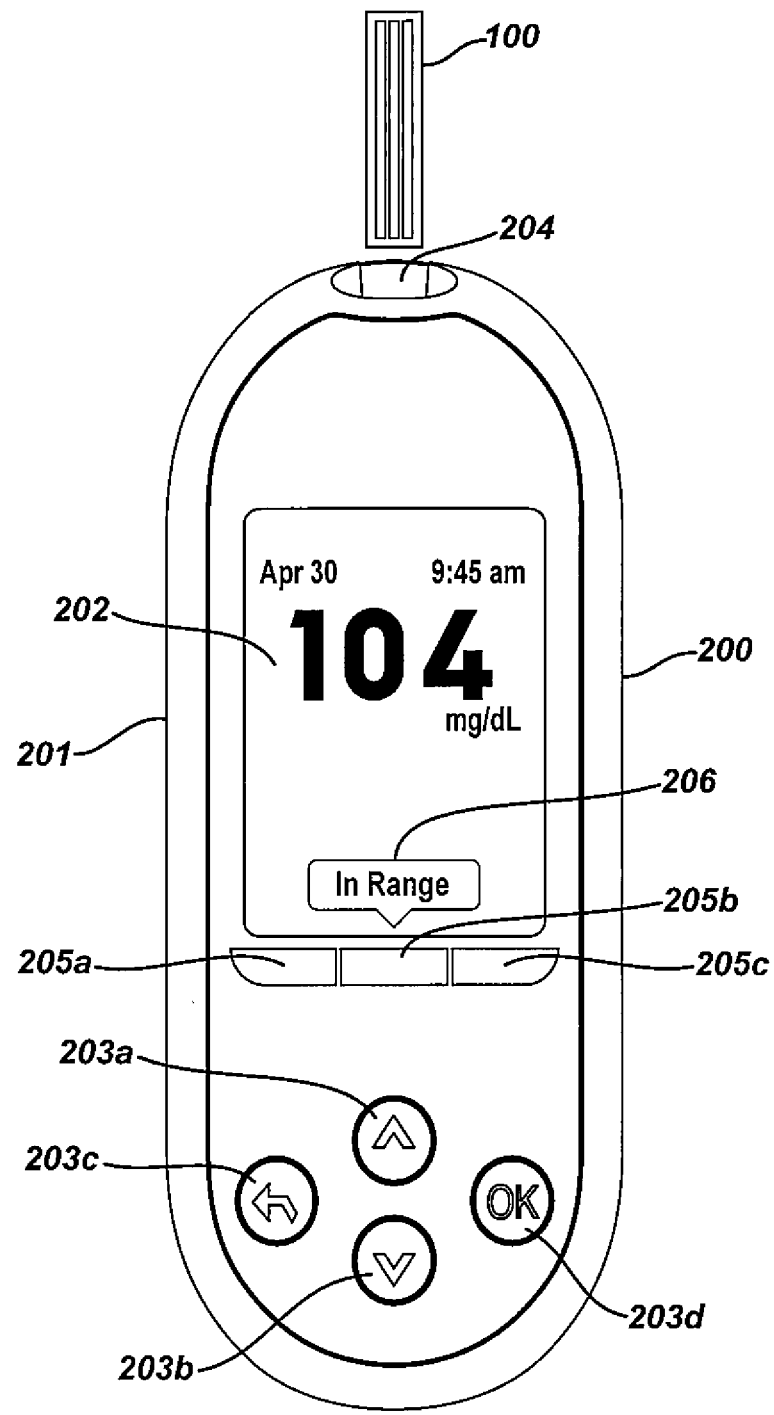
FIG. 1 illustrates a preferred blood glucose measurement system.

FIG. 1 illustrates a diabetes management system that includes a biosensor 100 and meter 200. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Figure 2:
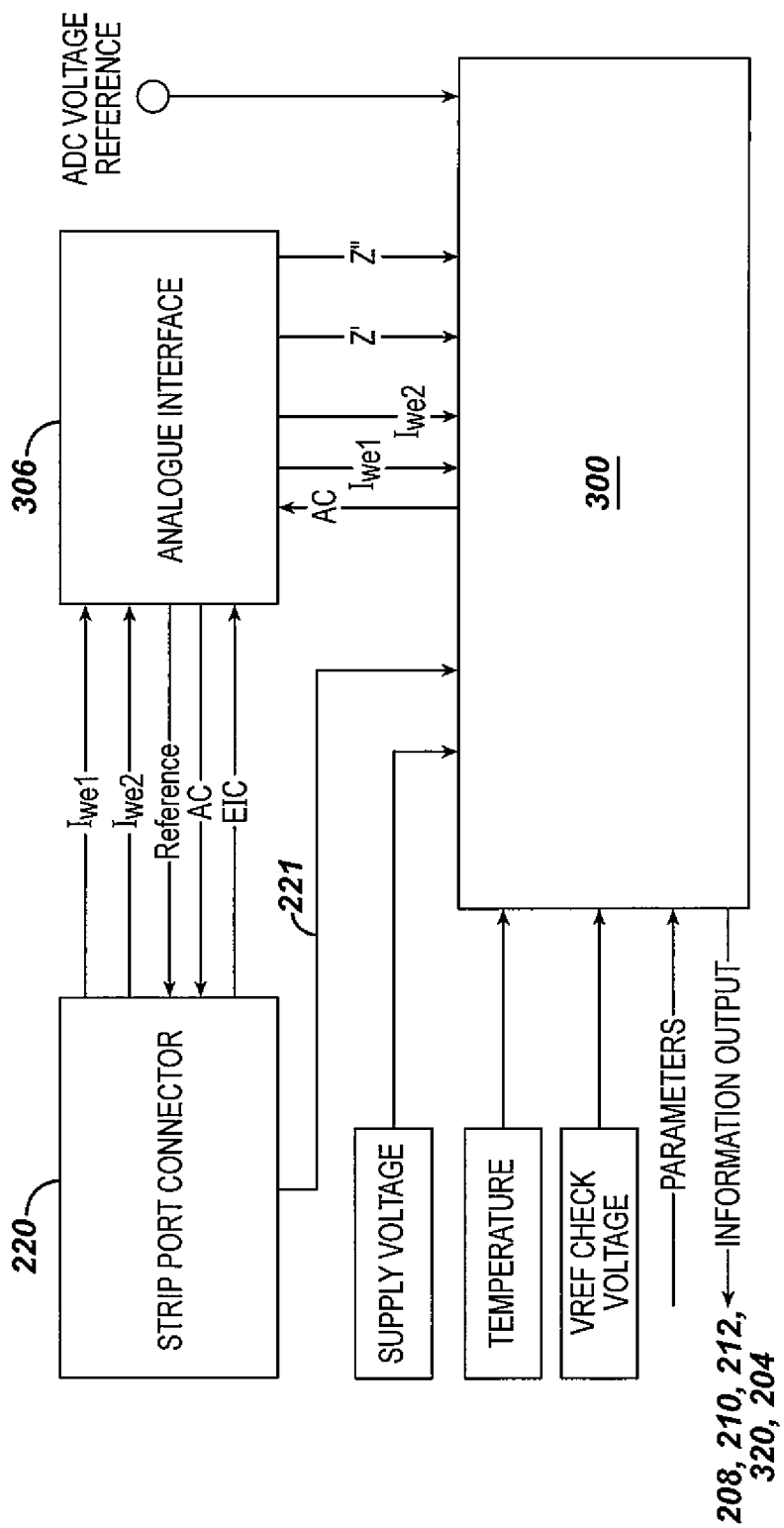
FIG. 2 illustrates in schematic the various components disposed in the meter of FIG. 1.

Referring back to FIG. 1, glucose meter or meter unit 200 may include a housing 201, display 202, user interface buttons ("up" or 203a; "down" or 203b; "back" or 203c and "ok" or 203d), and a strip port opening 204 for strip port connector 220 (FIG. 2). User interface buttons (203a-203d) may be configured to allow the entry of data, navigation of menus, and execution of commands. User interface button may be in the form of a two way toggle switch. Data may include values representative of analyte concentration, or information, which are related to the everyday lifestyle of an individual. Information, which is related to the everyday lifestyle, may include food intake, medication use, occurrence of health check-ups, and general health condition and exercise levels of an individual. The electronic components of meter 200 may be disposed on a circuit board that is within housing 201.

FIG. 2 illustrates (in simplified schematic form) the electronic components for the meter of FIG. 1. In FIG. 2, a strip port connector 220 is connected to the analogue interface 306 by five communication lines including an impedance sensing line EIC to receive signals from physical characteristic sensing electrode(s), alternating signal line AC driving signals to the physical characteristic sensing electrode(s), reference line for a reference electrode, and signal sensing lines from respective working electrode 1 and working electrode 2. A strip detection line 221 can also be provided for the connector 220 to indicate insertion of a test strip. The analog interface 306 provides four inputs to the processor 300: (1) real impedance Z'; (2) imaginary impedance Z"; (3) signal sampled or measured from working electrode 1 of the biosensor or $I_{we1}$; (4) signal sampled or measured from working electrode 2 of the biosensor or $I_{we2}$. There is one output from the processor 300 to the interface 306 to drive an oscillating signal AC of any value from 25 kHz to about 250 kHz or higher to the physical characteristic sensing electrodes. A phase differential P (in degrees) can be determined from the real impedance Z' and imaginary impedance Z". Microcontroller 300 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Figure 3:
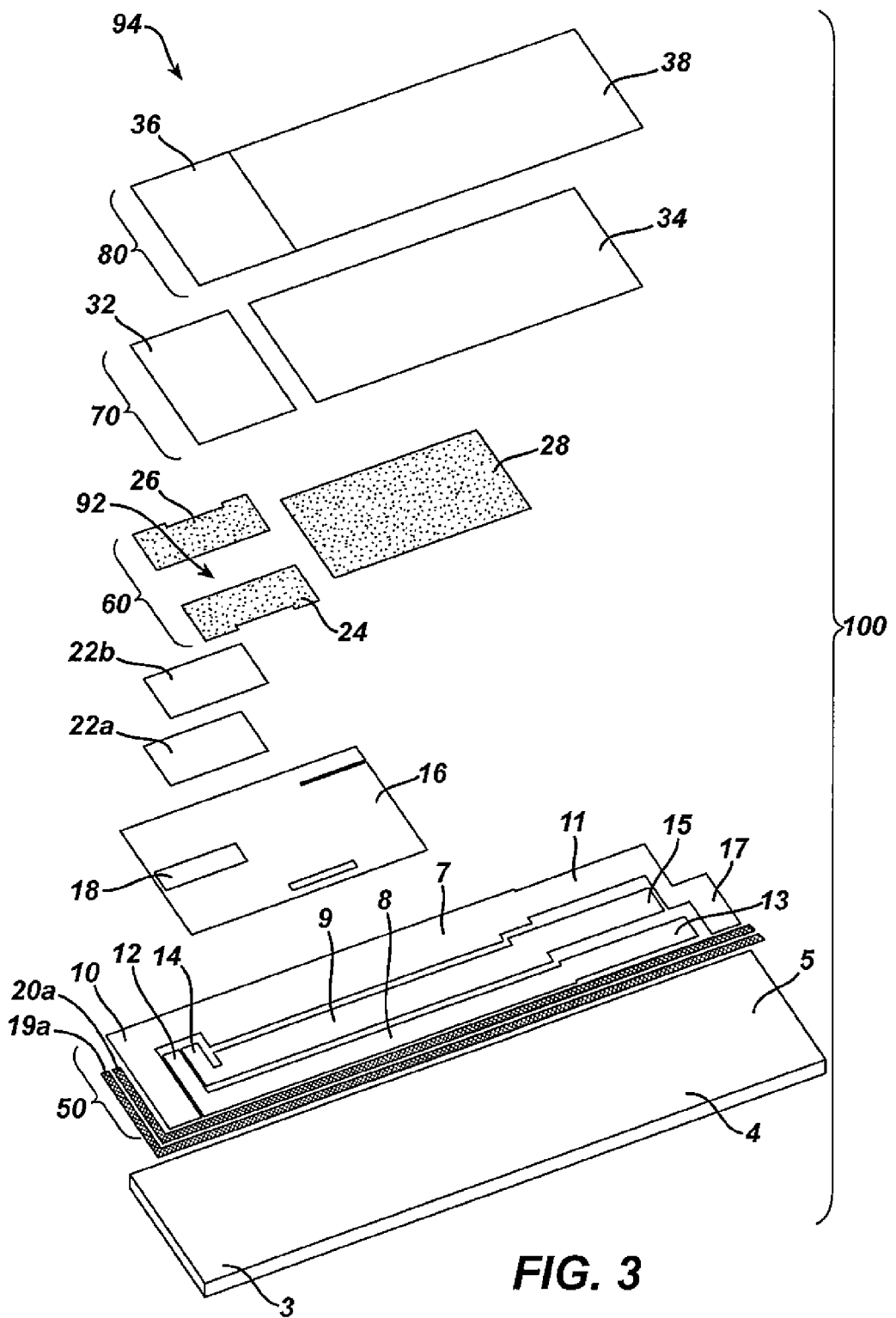
FIG. 3 illustrates a biosensor in an exploded view.

FIG. 3 is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3.

For test strip 100, as illustrated in FIG. 3, first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3. Details of the meter and strip are shown and described in related patent application Ser. Nos. 61/581,087; 61/581,089; 61/581,099; and 61/581,100, all filed on the same day of Dec. 29, 2011, U.S. Provisional Patent Application Ser. No. 61/654,013, filed on 31 May 2012; and International Patent Application PCT/GB2012/053279, PCT/GB2012/053277, and PCT/GB2012/053276, filed Dec. 28, 2012, (hereafter "Related Applications"), all the Related Applications are hereby incorporated by reference as if set forth herein with a copy of PCT/GB2012/053276 attached hereto as an Appendix.

Referring back to FIG. 1, the meter 200 is provided with indicia 205a, 205b and 205c to inform the user of the status of the blood glucose measurement using an indicator 206. The indicator 206 is part of the display and is controlled depending on the parameters for the range of a particular type of glucose measurements made. The range indicator 206 is a feature that designates a specific color to a Blood Glucose (BG) reading when it is displayed on the meter. The color is based on a range that is set up by the user. This range helps the user to know which numbers are "in-range" or good and which are "out of range" and therefore undesirable. Based on this logic, when indicator 206 points to indicia 205b (or green), the measurement is associated with In-Range readings. When indicator 206 points to indicia 205c (Red), this indicates that the measurement made is an Above Range reading. When indicator 206 points to indicia 205a (Blue), this means that the measurement is a Below Range reading. The blood glucose meter at any point can have 3 different range types for each of the categories of "pre-meal" and "post-meal" ranges. These different range types and their associated default have a "low limit" value of 70 mg/dL and "high limit" value of 180 mg/dL. It should be noted also that the general range (between 70 mg/dL and 180 mg/dL) that the meter is provided by default also has this general range.

Where the user has enabled flagging or tagging for the glucose measurements made with respect to before a meal or after meal, default limits are provided such as, for example, the "low limit" for before meal being about 70 mg/dL with "high limit" for before meal measurements being about 130 mg/dL, whereas for after meal measurements, the "low limit" is about 120 mg/dL and "high limit" is about 180 mg/dL.

Under certain circumstances, these default ranges may not be suitable for certain users due to the unpredictable nature of the diabetes. In such circumstances, the users are able to change the ranges. Applicants have realized that there are instances where the users may set the ranges in a manner that may cause the indicator 206 to provide inappropriate indication of the measurement.

Figure 4:
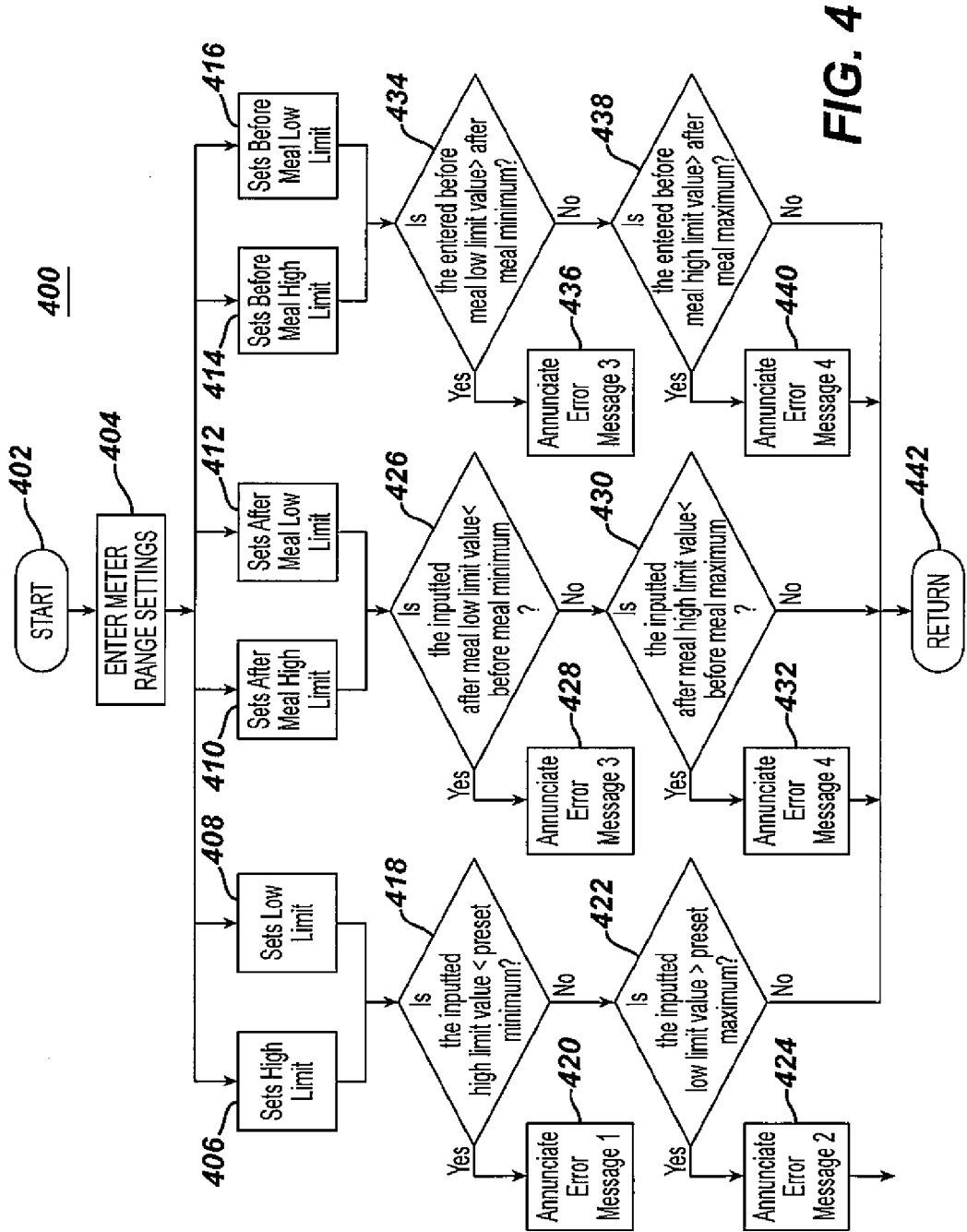
FIG. 4 is an exemplary logic diagram for determining a suitable setting of the various ranges provided in the preferred system.

As such, applicants have devised a technique to ensure that the settings of ranges are appropriate for use with the range indicator 206 of meter 200. One embodiment of the technique is shown here as logical process 400 in FIG. 4. In brief, the logical process has three guiding principles:

(1) when the user tries to set the "high limit" of a range less than the "low limit" of the range, then the "low limit" value will automatically reduce by one value less than the "high limit" to ensure that the "high limit" is greater than the "low limit". This will continue until the "low limit" value reaches the maximum permissible low. On the other hand, if the user sets the "low limit" higher than the "high limit", then the "high limit" value will automatically increment by one number greater than the "low limit" up until the maximum permissible "high limit" value is reached;

(2) The "after-meal low limit" cannot be set lower than the before-meal "low limit". If the user tries to do so, a warning message will be generated and the user will be asked to reset the "after-meal low limit" to a value greater than the before-meal "low limit". Similarly if the user tries to set a "before-meal low limit" higher than the "after-meal low limit", then a warning message shall be generated asking the user to reset the "before-meal low limit" to a value less than the "after-meal low limit";

(3) The "after-meal high limit" cannot be set lower than the before-meal "high limit". If the user tries to do so, a warning message will be generated and the user will be asked to reset the "after-meal high limit" to a value greater than the before-meal "high limit". Similarly if the user tries to set a before-meal "high limit" higher than the "after-meal high limit", then a warning message shall be generated asking the user to reset the "before-meal high limit" to a value less than the "after-meal high limit".

In particular, logic process 400 (FIG. 4) is utilized in the operation of the meter 200 and preferably is configured during initial setup of the meter or at any time desired by the user. Process 400 starts at step 402 which, as part of the meter setup utility 404, the user can navigate using the interface buttons or touchscreen in order to set up the upper and lower limits for each of the general glycemic range (steps 406 and 408), after meal glycemic range (steps 410 and 412) and before meal glycemic range (steps 414 and 416).

After setup in steps 406-416, the following steps 418-440 are carried out to ensure that applicants' inventive tripartite guiding principles are adhered to. Specifically, at step 418, a query is made as to whether the inputted high limit value is less than the preset (or previously reset) minimum. If true, a first error message is annunciated to the user at step 420. On the other hand, if the query at step 418 is false, then another query is made at step 422. At step 422, a query is made to determine whether the value entered by the user is greater than the preset (or previously reset) maximum. If true, the meter annunciates a second error message at step 424. If the query 422 is false, the logic returns to the main routine or to the remaining queries (426, 430, 434, and 438). As an example, if the user sets the "low-limit" of a particular range to 70 mg/dL and tries to set the "high limit" to 69 mg/dL, then the preset low limit will automatically decrease to a lower value such as, for example, 68 mg/dL. This will continue until the low-limit of the range reaches its lowest limit possible.

At step 426, a query is made as to whether the value entered by the user as an after-meal low limit is less than the preset (or previously set) before-meal minimum. If true, the system annunciates a third error message and if false, the logic proceeds to step 430. At step 432, the message may include a description that an after-meal low limit lower than the before-meal low limit. At step 430, a query is made as to whether the value entered by the user for the after-meal high limit is less than the preset (or previously reset) before-meal maximum. If the query 430 returns a true then a fourth message is annunciated and if false, the logic returns to the main routine or to the remaining queries (434 and 438). The fourth message may indicate a description that an after-meal high limit cannot be set to be lower than the before-meal high limit.

At step 434, a query is made as to whether the value entered by the user for a before-meal low limit is greater than a preset (or previously reset) after-meal minimum. If true at query 434, a fifth error message is annunciated at step 436, and if false, another query is made at step 438. At step 436, the message may include a description to the effect that the before-meal low limit cannot be higher than the after-meal low limit. At step 438, a query is made to determine whether the value entered by the user for the before-meal high limit is greater than the after-meal maximum. If true, the system annunciates a sixth error message at step 440 otherwise if false, the system returns to the main routine. At step 440, the error message may include a description that the before-meal high limit cannot be set to be greater than the after-meal high limit.

The guiding principles devised by applicants are to ensure that the user does not set ranges that overlap and potentially causing the range indicator 206 to indicate that the measured glucose in question is in the wrong range. In other words, the principles devised by applicants are intended to prevent the user from setting overlapping ranges thereby causing an incorrect range indication to be associated with the subject glucose measurement.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of visually indicating different glycemic states of a user for one or more different glycemic ranges of glucose values by automatically adjusting the one or more different glycemic ranges of glucose values of the glucose meter, the glucose meter having a user interface and a display operatively connected to a microprocessor and non-volatile memory, the one or more different glycemic ranges comprising a general glycemic range of glucose values varying between a general preset minimum value and a general preset maximum value, and the method comprising the steps of:
    entering into the microprocessor via the user interface of the glucose meter at least one of an input low value or an input high value to define the general glycemic range of glucose values;
    adjusting and storing the general preset minimum value of the general glycemic range in the non-volatile memory of the glucose meter, responsive to the input high value being less than the general preset minimum value, by setting the general preset minimum value to a new low value, the new low value being lower than the input high value or equal to a minimum permitted low value;
    adjusting and storing the general preset maximum value of the general glycemic range in the non-volatile memory of the glucose meter, responsive to the input low value being greater than the general preset maximum value, by setting the general preset maximum value to a new high value greater than the input low value or equal to a maximum permitted high value; and
    responsive to a glucose measurement of the user with the glucose meter being in the general glycemic range stored in the non-volatile memory of the glucose meter, visually indicating a general glycemic state of the user from among the different glycemic states with a common visual indicator key.

2. A method of visually indicating different glycemic states of a user for one or more different glycemic ranges of glucose values by automatically adjusting the one or more different glycemic ranges of glucose values of the glucose meter, the glucose meter having a user interface and a display operatively connected to a microprocessor and non-volatile memory, the one or more different glycemic ranges comprising an after meal glycemic range of glucose values varying between an after meal low value and an after meal high value, and the method comprising the steps of:
    entering into the microprocessor via the user interface of the glucose meter at least one of the after meal low value for an after meal minimum and the after meal high value for an after meal maximum to define the after meal glycemic range of glucose values;
    responsive to the after meal low value being lower than a before meal minimum, annunciating an error and requesting the user via the user interface to change the after meal low value to a value higher than the before meal minimum and storing the after meal low value in the non-volatile memory of the glucose meter;
    responsive to the after meal high value being lower than a before meal maximum, annunciating an error and requesting the user via the user interface to change the after meal high value to a value greater than the before meal maximum and storing the after meal high value in the non-volatile memory of the glucose meter; and
    responsive to a glucose measurement of the user with the glucose meter being in the after meal glycemic range stored in the non-volatile memory of the glucose meter, visually indicating an after meal glycemic state of the user from among the different glycemic states with a common visual indicator key.

3. A method of visually indicating different glycemic states of a user for one or more different glycemic ranges of glucose values by automatically adjusting the one or more different glycemic ranges of glucose values of the glucose meter, the glucose meter having a user interface and a display operatively connected to a microprocessor and non-volatile memory, the one or more different glycemic ranges comprising a before meal glycemic range of glucose values varying between a before meal low value and a before meal high value, and the method comprising the steps of:
    entering into the microprocessor via the user interface of the glucose meter at least one of the before meal low value for a before meal minimum and the before meal high value for a before meal maximum to define the before meal glycemic range of glucose values;
    responsive to the before meal low value being higher than an after meal minimum, annunciating an error and requesting the user via the user interface to change the before meal low value to a value less than the after meal minimum and storing the before meal low value in the non-volatile memory of the glucose meter;
    responsive to the before meal high value being higher than the after meal maximum, annunciating an error and requesting the user via the user interface to change the before meal high value to a value less than the after meal maximum and storing the before meal high value in the non-volatile memory of the glucose meter; and
    responsive to a glucose measurement of the user with the glucose meter being in the before meal glycemic range stored in the non-volatile memory of the glucose meter, visually indicating a before meal glycemic state of the user from among the different glycemic states with a common visual indicator key.

4. The method of claim 1, wherein the one or more glycemic ranges further comprise an after meal glycemic range of glucose values varying between an after meal low value and an after meal high value, and the method further comprises the steps of:
    entering into the microprocessor via the user interface of the glucose meter at least one of an after meal low value for an after meal minimum and an after meal high value for an after meal maximum to define the after meal glycemic range of glucose values;
    responsive to the after meal low value being lower than a before meal minimum, annunciating an error and requesting the user via the user interface to change the after meal low value to a value higher than the before meal minimum and storing the after meal low value in the non-volatile memory of the glucose meter;
    responsive to the after meal high value being lower than a before meal maximum, annunciating an error and requesting the user via the user interface to change the after meal high value to a value greater than the before meal maximum and storing the after meal high value in the non-volatile memory of the glucose meter; and
    responsive to the glucose measurement of the user with the glucose meter being in the after meal glycemic range stored in the non-volatile memory of the glucose meter, visually indicating an after meal glycemic state of the user from among the different glycemic states with the common visual indicator key.

5. The method of claim 4, wherein the one or more glycemic ranges further comprise a before meal glycemic range of glucose values varying between a before meal low value and a before meal high value, and the method further comprises the steps of:
    entering into the microprocessor via the user interface of the glucose meter at least one of a before meal low value for a before meal minimum and a before meal high value for a before meal maximum to define the before meal glycemic range of glucose values;
    responsive to the before meal low value being higher than the after meal minimum, annunciating an error and requesting the user via the user interface to change the before meal low value to a value less than the after meal minimum and storing the before meal low value in the non-volatile memory of the glucose meter;
    responsive to the before meal high value being higher than the after meal maximum, annunciating an error and requesting the user via the user interface to change the before meal high value to a value less than the after meal maximum and storing the before meal high value in the non-volatile memory of the glucose meter; and
    responsive to the glucose measurement of the user with the glucose meter being in the before meal glycemic range stored in the non-volatile memory of the glucose meter, visually indicating a before meal glycemic state of the user from among the different glycemic states with the common visual indicator key.

6. The method of claim 1, wherein the one or more glycemic ranges further comprise a before meal glycemic range of glucose values varying between a before meal low value and a before meal high value, and the method further comprises the steps of:
    entering into the microprocessor via the user interface of the glucose meter at least one of a before meal low value for a before meal minimum and a before meal high value for a before meal maximum to define the before meal glycemic range of glucose values;
    responsive to the before meal low value being higher than an after meal minimum, annunciating an error and requesting the user via the user interface to change the before meal low value to a value less than the after meal minimum and storing the before meal low value in the non-volatile memory of the glucose meter;
    responsive to the before meal high value being higher than the after meal maximum, annunciating an error and requesting the user via the user interface to change the before meal high value to a value less than the after meal maximum and storing the before meal high value in the non-volatile memory of the glucose meter; and
    responsive to the glucose measurement of the user with the glucose meter being in the before meal glycemic range stored in the non-volatile memory of the glucose meter, visually indicating a before meal glycemic state of the user from among the different glycemic states with the common visual indicator key.

7. The method of claim 2, wherein the one or more glycemic ranges further comprise a before meal glycemic range of glucose values varying between a before meal low value and a before meal high value, and the method further comprises the steps of:
    entering into the microprocessor via the user interface of the glucose meter at least one of a before meal low value for a before meal minimum and a before meal high value for a before meal maximum to define the before meal glycemic range of glucose values;
    responsive to the before meal low value being higher than an after meal minimum, annunciating an error and requesting the user via the user interface to change the before meal low value to a value less than the after meal minimum and storing the before meal low value in the non-volatile memory of the glucose meter;
    responsive to the before meal high value being higher than the after meal maximum, annunciating an error and requesting the user via the user interface to change the before meal high value to a value less than the after meal maximum and storing the before meal high value in the non-volatile memory of the glucose meter; and
    responsive to the glucose measurement of the user with the glucose meter being in the before meal glycemic range stored in the non-volatile memory of the glucose meter, visually indicating a before meal glycemic state of the user from among the different glycemic states with the common visual indicator key.

\* \* \* \* \*